United States Patent [19]
Cohen

[11] Patent Number: 5,356,288
[45] Date of Patent: Oct. 18, 1994

[54] DUAL ORTHODONTIC BRACKET

[76] Inventor: Howard Cohen, 339 Forest Ave., Woodmere LI, N.Y. 11598

[21] Appl. No.: 987,458

[22] Filed: Dec. 7, 1992

[51] Int. Cl.$^5$ .............................................. A61C 3/00
[52] U.S. Cl. ..................................... 433/8; 433/10; 433/13; 433/14; 433/15
[58] Field of Search ............... 433/8, 9, 10, 11, 13, 433/14, 15, 16, 17, 20

[56] References Cited

U.S. PATENT DOCUMENTS

| | | | |
|---|---|---|---|
| 2,019,773 | 11/1935 | Wirt | 433/11 |
| 2,759,265 | 8/1956 | Johnson | 433/13 |
| 3,408,739 | 11/1968 | Johnson | |
| 3,464,112 | 9/1969 | Silverman et al. | 433/11 |
| 3,729,826 | 5/1973 | Kesling | 433/13 |
| 3,780,437 | 12/1973 | Wildman | 433/14 |
| 3,838,514 | 10/1974 | Polak | 433/8 X |
| 4,209,906 | 7/1980 | Fujita | 433/11 |
| 4,227,876 | 10/1980 | Fogel et al. | 433/11 |
| 4,242,085 | 12/1980 | Wallshein | 433/14 |
| 4,249,897 | 2/1981 | Anderson | 433/8 |
| 4,268,249 | 5/1981 | Forster | 433/10 |
| 4,302,532 | 11/1981 | Wallsheim | 433/8 |
| 4,386,909 | 6/1983 | Hanson | 433/20 |
| 4,427,381 | 1/1984 | Hall | 433/14 |
| 4,522,590 | 6/1985 | Pletcher | 433/15 |
| 4,523,908 | 6/1985 | Drisaldi et al. | 433/8 |
| 4,527,975 | 7/1985 | Ghafari et al. | 433/8 |
| 4,531,911 | 7/1985 | Creekmore | 433/8 |
| 4,585,413 | 4/1986 | Wool | 433/8 |
| 4,634,622 | 1/1987 | Rosenberg | 433/10 |
| 4,712,999 | 12/1987 | Rosenberg | 433/8 |
| 4,799,882 | 1/1989 | Kesling | 433/8 |
| 4,842,512 | 6/1989 | Kesling | 433/8 |
| 4,859,179 | 8/1989 | Kesling | 433/8 |
| 4,877,398 | 10/1989 | Kesling | 433/8 |
| 4,941,825 | 7/1990 | Lerner | 433/14 |
| 5,037,297 | 8/1991 | Lerner | 433/14 |
| 5,098,288 | 3/1992 | Kesling | 433/9 |

FOREIGN PATENT DOCUMENTS

1428674 3/1976 United Kingdom ................ 433/13

Primary Examiner—Gene Mancene
Assistant Examiner—Nicholas D. Lucchesi
Attorney, Agent, or Firm—Robert W. Fiddler

[57] ABSTRACT

This invention relates to a novel bracket assembly for producing tooth movement in the treatment of dental malocclusions. A dual bracket system includes a primary and secondary bracket. An archwire is received in the secondary bracket. The primary bracket is attached to the tooth and the secondary bracket engages the primary bracket, thereby holding the secondary bracket and the archwire in place. Various configurations of the secondary bracket can be used with the primary bracket for producing desired tooth movements. A novel pin and ligature assembly can be used with the bracket assembly or a conventional bracket.

10 Claims, 9 Drawing Sheets

DUAL ORTHODONTIC BRACKET

BACKGROUND OF THE INVENTION

1. Field of the Invention

This invention relates to an improved method and apparatus for producing tooth movement in the treatment of dental malocclusions.

2. Description of the Related Art

Conventional orthodontic techniques include edgewise and Begg. It is recognized that the Begg bracket is very similar to the pin and tube appliance introduced by Dr. Angle in 1910, but is inverted. In 1925, Dr. Angle removed the vertical pin slot from the bracket and cut an archwire slot in its face and added an extension (wing) to its gingival portion. This resulted in three dimensional tooth control. Dr. Angle saw limitations of his new edgewise bracket and suggested placing brackets at angles so that the insertion of straight archwires would tip the crowns. This concept eventually led to the development of the "straight wire" brackets that have torque and uprighting built into the archwire slots as well as in some instances rotational forces and labial lingual forces.

Straight wire brackets have the disadvantage that torquing, up-righting and rotation built into these brackets cannot satisfy the requirements for the correct final position of all teeth. The teeth in some instances may be over-torqued, up-righted over-rotated or placed too far lingually or buccally. In other instances, built-in torquing, up-righting or rotation angulations or other tooth movements of the straight wire brackets are less than needed. In both of the above situations, the orthodontist is required to use auxiliaries such as torquing wires, up-righting springs, place bends in the archwires or, lastly, change the entire bracket and replace it with a bracket having the necessary angulations for the final precise and correct placement of the teeth.

U.S. Pat. No. 3,408,739 describes a modification of the Begg technique including a vertically extending archwire slot which allows free tipping of teeth during treatment as compared to the edgewise brackets. Edgewise brackets have been described which provide tipping means when force is applied, as shown in U.S. Pat. Nos.: 4,842,512; 4,859,179; and 4,877,398. U.S. Pat. Nos. 4,227,876 and 4,242,085 disclose combination brackets having both labially or horizontally facing horizontal archwire slots and gingivally facing vertical archwire slots. In addition, U.S. Pat. No. 4,427,381 describes converting a Begg bracket into an edgewise bracket by the addition of attachments.

The brackets previously described have the disadvantage that they do not always function as desired. Also, the brackets are often cumbersome and unesthetic. In addition, it is necessary for the orthodontist to have a large inventory of brackets and many archwire changes for correction of dental malocclusions which is costly in both time and money to the orthodontist and oftentimes causes discomfort to the patient.

U.S. Pat. Nos. 4,799,882 and 5,098,288 describe brackets which have an improved esthetic appearance by using porcelain or plastic or in combination.

U.S. Pat. No. 4,303,532 describes using metal inserts in plastic brackets in order to overcome deformation of the plastic brackets when orthodontic forces are applied. These protective metal liners make the bracket larger and more unesthetic as the archwire is inserted from the labial surface and is clearly visible as is the metal liner.

Of possible general relevance to the invention are U.S. Pat. Nos.: 4,209,906; 4,268,249; 4,522,590; 4,523,908; 4,634,662 and 4,712,999 describing means for holding the archwire in place.

SUMMARY OF THE INVENTION

Briefly described, the invention comprises a dual bracket system including a primary bracket and a secondary bracket. The present invention allows for the selective application of forces to any one tooth or teeth, as desired, in a manner that has less potential to damage the teeth being moved and surrounding tissues as compared to existing brackets and methods. Also, the invention is easy, time efficient and less costly than conventional brackets and methods.

In a preferred embodiment the orthodontic bracket system in accordance with the present invention includes a secondary bracket within a primary bracket. The primary bracket is attached to a base and the base is preferably attached to a surface of a tooth by an adhesive. The secondary bracket engages the primary bracket. In accordance with the preferred embodiment, the secondary bracket holds an archwire and both the secondary bracket and the archwire are held by the primary bracket, thereby eliminating the need for pins or steel and elastic ties or other means of ligation to hold the archwire in place. Various configurations of the secondary bracket can be used with the primary purpose of providing predetermined tooth movements. In addition, an archwire slot can be angled to receive and lock in place the archwire. The primary bracket and the secondary bracket, called the dual orthodontic module, can be formed of metal, plastic, ceramic, polymer or any combination. Such combinations are beneficial for bracket strength and esthetics.

A novel pin and ligature assembly can be used with the bracket system of the present invention and with conventional brackets which include a vertical slot. In addition, if the orthodontist chooses to use the primary bracket without the engaged secondary bracket, the pin and ligature assembly can also be used to hold the archwire in an archwire slot of the primary bracket. In the pin and ligature assembly, the ligature is stretched over either the primary bracket or both the primary and second brackets and engages the primary bracket. Preferably, the pin of the pin and ligature assembly includes a biasing means for engaging either the vertical slot of the primary bracket and/or the secondary bracket of the present invention or the vertical slot of a conventional bracket.

DETAILED DESCRIPTION OF THE DRAWINGS

DETAILED DESCRIPTION OF THE INVENTION

During the course of this description, like numbers will be used to identify like elements according to the different figures which illustrate the invention.

In orthodontic terms "tipping" refers to either labial/lingual or mesial/distal movement of the crown and root of the tooth and/or teeth in combination respectively. Tipping of the teeth is the most gentle movement and forces applied to cause tipping tend to decrease any damage to the roots and surrounding bone and tissues of the tipped teeth. The term "uprighting" refers to either mesial or distal movement of the crown or crowns and the root or roots of the tooth or teeth to be moved. Another term commonly used is "torque", which refers to the movement of a tooth, either the crown or the root, in a labial/lingual direction as a result of forces applied to either the crown or root of the tooth respectively. Finally, the term "bodily movement" refers to the movement of the tooth, both roots and crowns, in the same direction at the same rate, eliminating the need for subsequent uprighting (tipping) or torquing. Another type of movement involves the application of forces so as to allow a tooth to move buccally or lingually.

Figure 1:
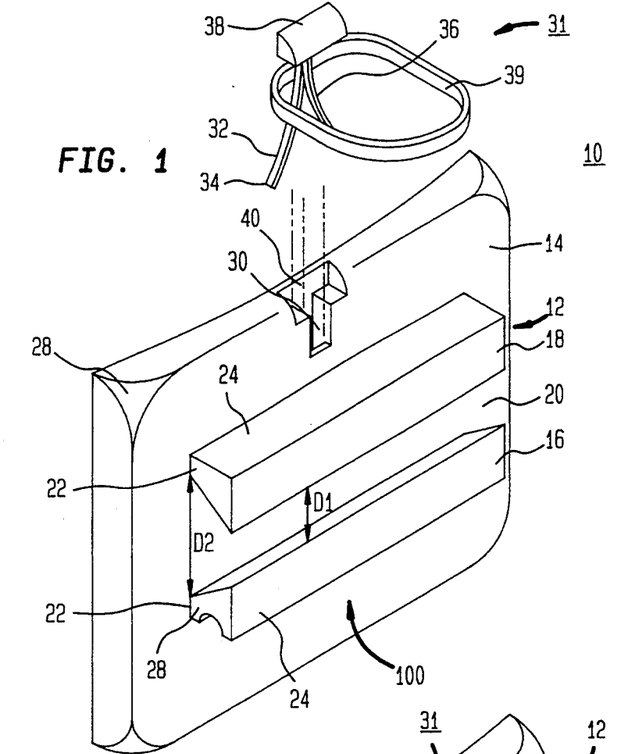
FIG. 1 is a front elevational perspective view of a primary bracket in accordance with the present invention.

As best seen in FIG. 1, the bracket assembly is formed with a primary bracket 12 having a pair of spaced preferably parallel holding members 16 and 18 forming an archwire holding slot 20 therebetween.

The transverse cross-sections of holding members 16 and 18 are angulated as seen in FIG. 1, so hat the distance $D_1$ between the front surfaces 24 is smaller than the distance $D_2$ between the rear surfaces of the holding members as a result of which the archwire slot 20 is narrower buccally and wider lingually to implement locking the secondary bracket in place.

Base 14 can include vertical slot 30 for receiving pin 32 of pin and ligature assembly 31. Pin 32 includes legs 34 and 36 which bias pin 32 in opening 30. Cover 38 is formed perpendicular to legs 34 and 36. Preferably, legs 34 and 36 are formed of a resilient material. Vertical slot 30 includes a recess for receiving cover 38. An elastic ligature 39 is attached to pin 32.

Figure 2:
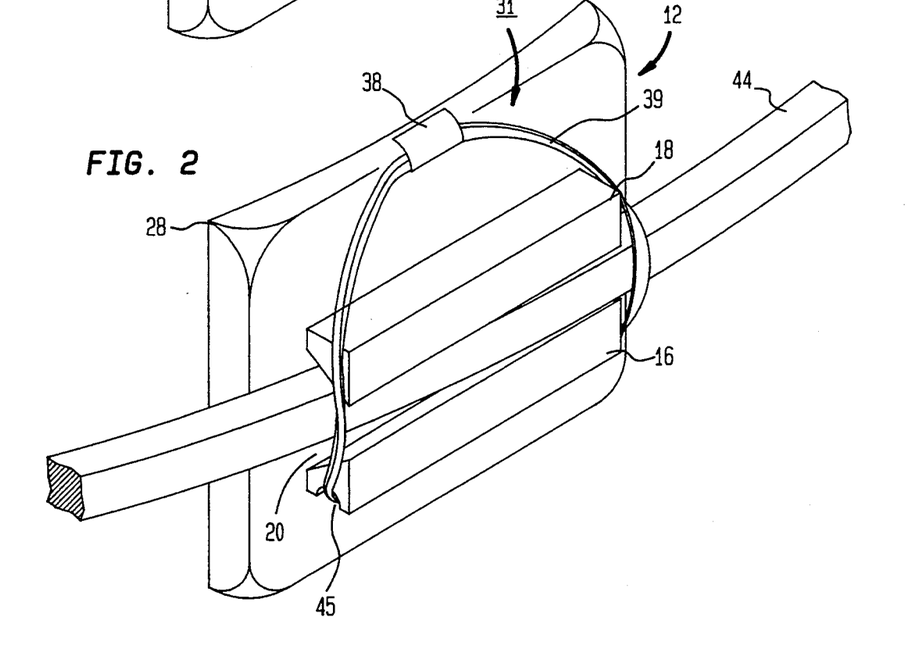
FIG. 2 is a front elevational perspective view of a primary bracket as shown in FIG. 1 after insertion of an archwire with a retaining pin/ligature assembly exploded therefrom.

FIG. 2 illustrates the use of pin and ligature assembly 31 with primary bracket 12. Archwire 44 is slidably inserted in archwire slot 20 between holding members 16, 18. After insertion of archwire 44, elastic ligature 39 is stretched around holding members 16 and 18 for holding archwire 44 in place. The bottom surface 45 of holding member 16 can be indented for receiving elastic ligature 39. It is known in the art that conventional ligature assemblies are attached to brackets by bending a pin around the ligature. Pin and ligature assembly 31 has the advantage of attaching a ligature to a bracket without bending a pin around the ligature.

Figure 3:
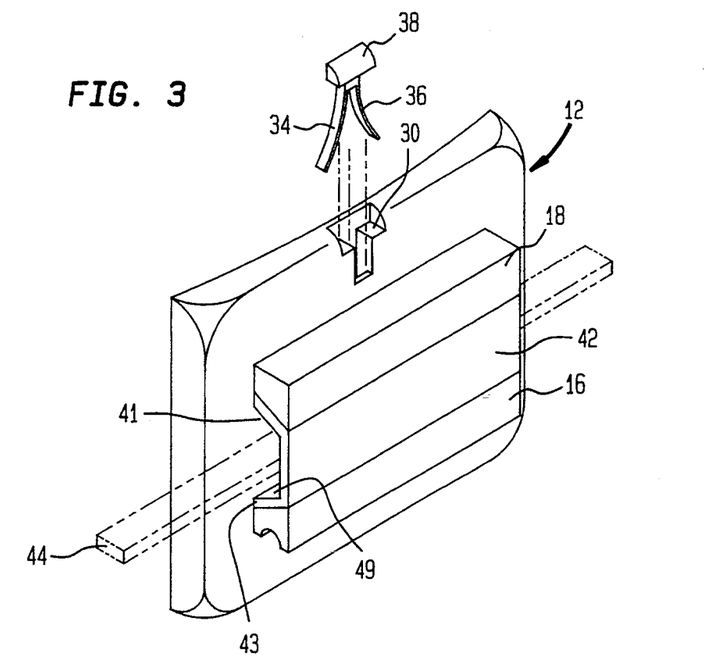
FIG. 3 is a front elevational perspective view of the dual orthodontic module including a secondary bracket engaged with the primary bracket and having an inserted archwire.

As best seen in FIG. 3, secondary bracket 42 is formed with an external contour which mates with the interior facing surfaces between members 16 and 18 so that the secondary bracket may either be slid or snapped between the retaining members 16 and 18. Secondary bracket 42 includes an opening 49 for slidably receiving archwire 44. Opening 49 opens toward rear surface 45 of secondary bracket 42 so that opening 49 faces the tooth. Opening 49 holds archwire 44 in place. Secondary bracket 42 eliminates the need for the use of a ligation for holding an archwire in place. An index identifying marking (not shown) can be formed on rear surface 45 of secondary bracket 42 facing the tooth. The index is not seen by an observer of the bracket.

As shown in FIG. 3, pin 32 including cover 38 and legs 34, 36 can be inserted into vertical slot 30 for covering the vertical slot so as to prevent debris from collecting in vertical slot 30. Preferably, the external surface of the primary bracket 12 and secondary bracket 42 is formed of a material that is highly esthetic such as plastic or ceramic for blending in with the surface of the tooth and for blending the primary bracket with the secondary bracket.

Figure 4:
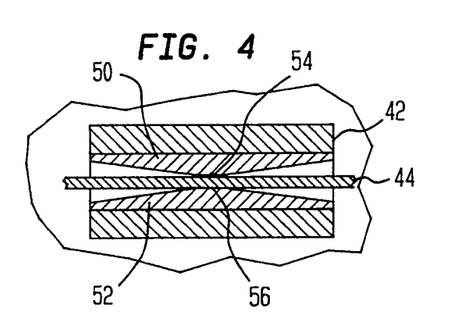
FIG. 4 is a cross-sectional view of a tapered secondary bracket.
Figure 5:
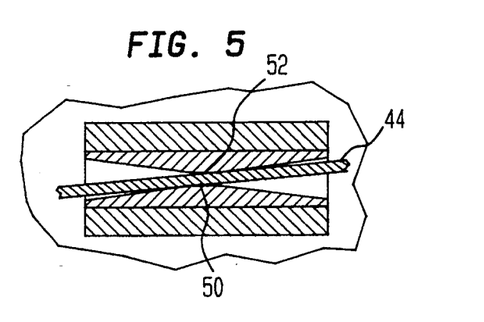
FIG. 5 is a cross-sectional view of the secondary bracket shown in FIG. 4 with an inserted archwire arranged for tipping movement.

FIG. 4 is a cross-sectional view of archwire 44 engaged with secondary bracket 42. Inner surfaces 50, 52 of secondary bracket 42 have tapered portions 54, 56 near the mid point of the surface for providing single point contact of archwire 44 with secondary bracket 42. Secondary bracket 42 with tapered portions 52, 54 provides unipoint contact to archwire 44 which is advantageous for tipping of teeth. For example, secondary bracket 42 can be used like bracket configurations. FIG. 5 illustrates the secondary bracket shown in FIG. 4 after a tipping movement is applied to archwire 44.

Figure 6:
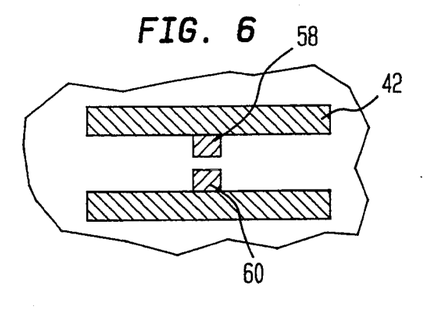
FIG. 6 is a cross-sectional view of the secondary bracket having shortened parallel contact members to hold the archwire.
Figure 7:
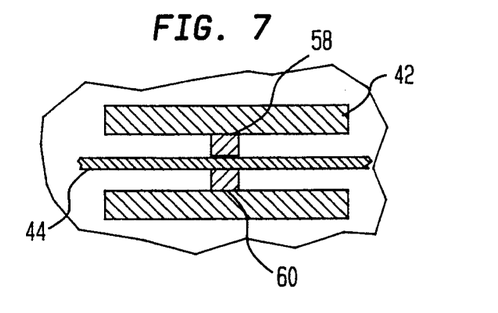
FIG. 7 is a cross-sectional view of the secondary bracket shown in FIG. 6 with an inserted archwire.

FIG. 6 illustrates a cross-sectional view of secondary bracket 42 including inner contact surfaces 58, 60. Archwire 44 is inserted between inner contact surfaces 58, 60, as illustrated in FIG. 7. Inner contact surfaces 58, 60 extend along a small portion of secondary bracket 42. Inner contact surfaces 58, 60 are advantageous for tipping movements of teeth.

Figure 8:
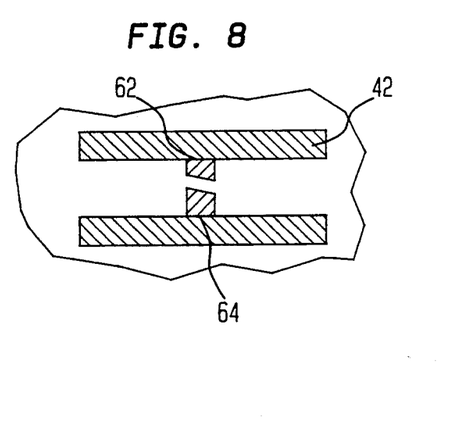
FIG. 8 is a cross-sectional view of the secondary bracket having shortened angled parallel contact members to hold the archwire.

FIG. 8 illustrates inner narrow contact surfaces 62 and 64. Inner contact surfaces 62, 64 include angled surfaces of a pre-determined angle for positioning teeth at a predetermined angle.

Figure 9:
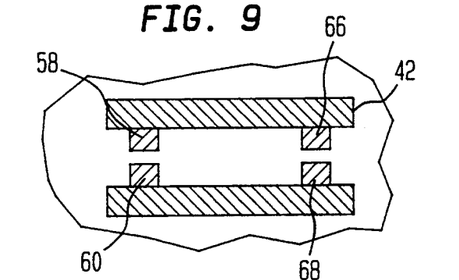
FIG. 9 is a cross-sectional view of the secondary bracket in which each of the parallel contact members includes a pair of shortened angled parallel contact members to hold the archwire.
Figure 10:
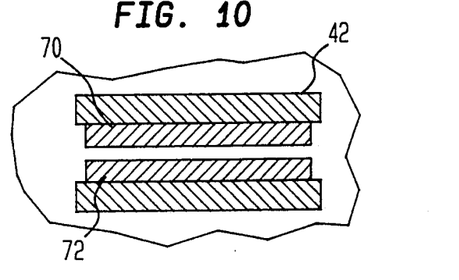
FIG. 10 is a cross-sectional view of the secondary bracket in which each of the parallel contact members includes a pair of parallel contact members along the length of the secondary bracket to hold the archwire.

FIG. 9 illustrates a pair of inner contact surfaces 58, 60 and 66, 68. An archwire can be inserted between the pair of contact surfaces, this pair is referred to in the art as "siamese". Preferably, the pair of surfaces provides bodily movement of the teeth with minimal frictional resistance. In the alternative, a pair of inner contact surfaces 70 and 72 can extend along the length of bracket 42 as shown in FIG. 10. Inner contact surfaces 70, 72 can be used for bodily movements of teeth and provides maximum frictional contact.

Figure 11:
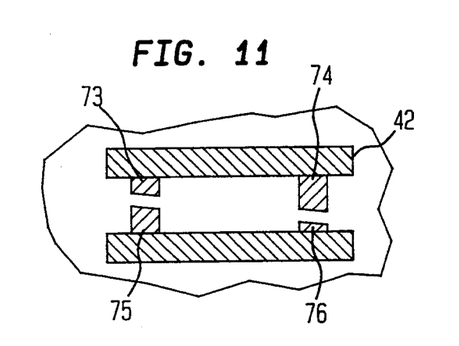
FIG. 11 is a cross-sectional view of the secondary bracket in which each of the parallel members includes a pair of shortened angled parallel contact members to hold the archwire.
Figure 12:
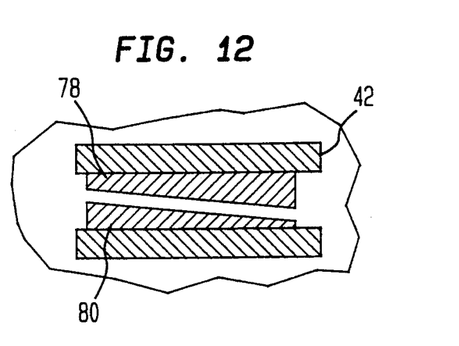
FIG. 12 is a cross-sectional view of the secondary bracket in which each of the parallel members includes a pair of angled parallel contact members along the length of the secondary bracket to hold the archwire.

FIG. 11 shows a pair of shortened angled parallel contact members 73, 75 and 74, 76 for preferably providing angulated bodily movements. Contact members 73,75, 74,76 are angulated at a predetermined angulation. Alternatively, angulated bodily movements can be obtained with angled parallel contact members 78, 80 which extend along the length of parallel holding members 16, 18, as shown in FIG. 12.

Figure 13:
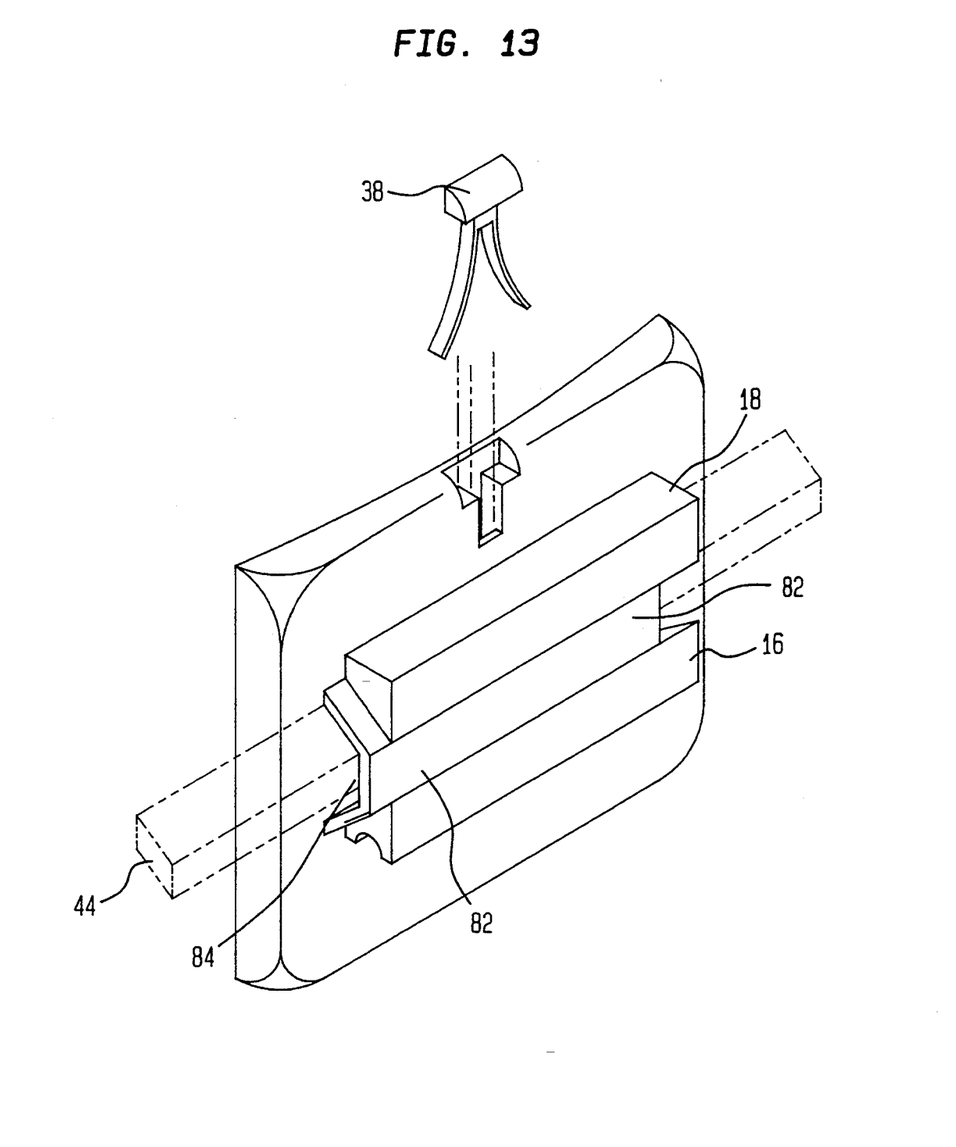
FIG. 13 is a front elevational view of a bracket assembly including an angled archwire slot to hold the archwire.

An increased angle of the archwire slot can be achieved with the embodiment shown in FIG. 13. Archwire slot 84 of secondary bracket 82 is angled. Preferably, archwire slot 84 can be upwardly or downwardly angled and/or mesially or distally angled at a predetermined angle from the horizontal. The different angulations of archwire slot 84 provide for different degrees of torquing, uprighting and rotating of the tooth.

Figure 14A:
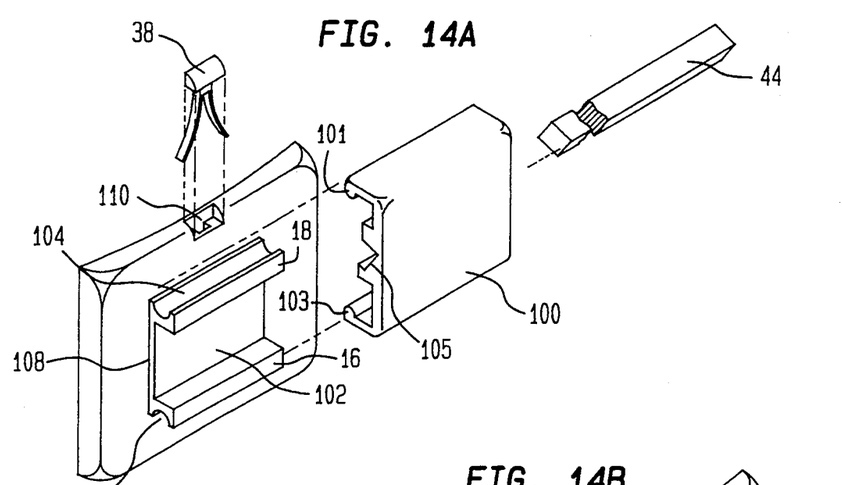
FIG. 14A is an exploded front elevational view showing the bracket system assembly with a secondary bracket forming a cover entirely covering the primary bracket.
Figure 14B:
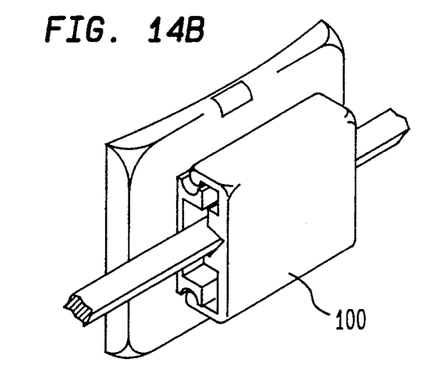
FIG. 14B is an exploded front elevational perspective view of the bracket assembly as show in FIG. 14 after insertion of the archwire within the second bracket and engagement of the secondary bracket with the primary bracket.
Figure 14C:
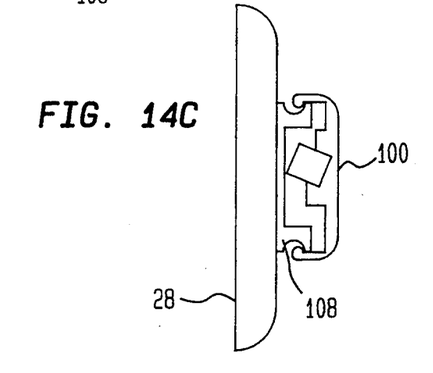
FIG. 14C is a side elevational view of the bracket assembly as shown in FIG. 14B.

FIGS. 14A–14C illustrate a secondary bracket 100 which covers primary bracket 108. Parallel holding members 16, 18 are arranged on either side of slot 105. Secondary bracket 100 includes parallel edges 101, 103 for slidably engaging ridges 104, 106 of holding members 16, 18. Slot 105 receives archwire 44. In this embodiment slot 105 is upwardly angulated.

Figure 15:
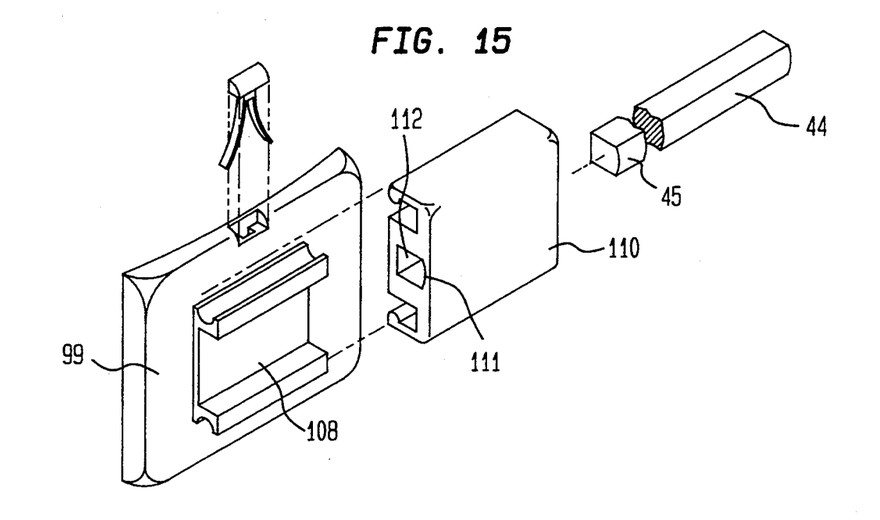
FIG. 15 is an exploded front elevational view showing the bracket system assembly with a secondary bracket forming a cover entirely covering the primary bracket and including in the form of a wire enclosing channel for holding an archwire

In the alternative, opening 111 can be formed as a duct extending parallel to edges 101 and 102, as shown in FIG. 15. Opening 111 can have a curved edge 111 for receiving curved edge 47 of archwire 44. Opening 111 surrounds archwire 44. Archwire 44 can be threaded into opening 111 before secondary bracket 110 is placed in the mouth and subsequently slid into primary bracket 99.

Figure 16:
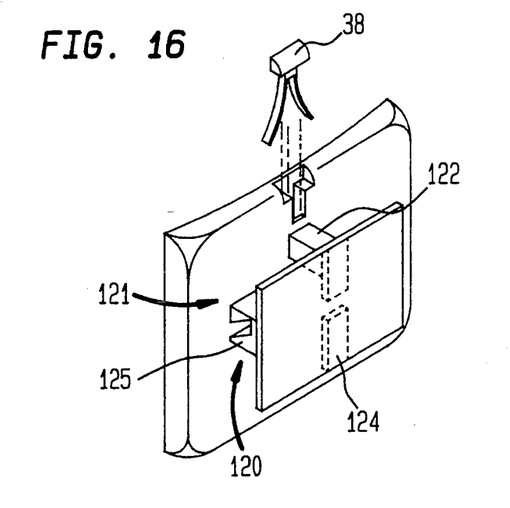
FIG. 16 is a front elevational perspective view of another form of bracket system assembly with a secondary racket covering the primary bracket.

FIG. 16 illustrates an alternative embodiment of secondary bracket 120 in which the primary bracket has a reduced width. Contact member 125 slides into engagement with holding members 122, 124 of primary bracket 121. Secondary bracket 120 is preferably used for torquing or uprighting or tipping when desired. Primary bracket 121 has the advantage of being smaller thereby being more comfortable in the mouth and possibly causing less obstructions.

Figure 17:
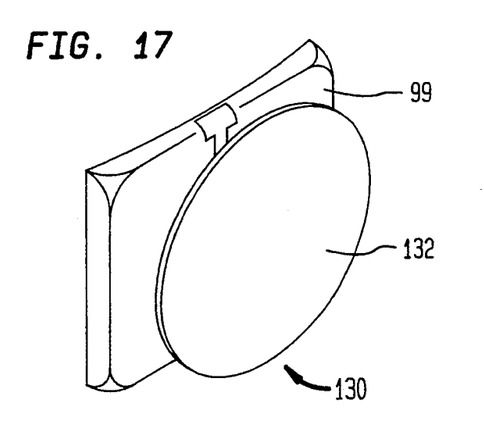
FIG. 17 is a perspective front elevational view of a bracket system assembly with secondary bracket including a circular contoured cover.

Secondary bracket 130 can have a circular shape for an aesthetic appearance, as shown in FIG. 17. In this embodiment, secondary bracket 130 can entirely cover primary bracket 99. Secondary bracket 130 includes a contoured surface 132 for matching the shape of the tooth. Contoured surface 132 can be circular, oval, elliptical or rhomboidical in shape. Preferably, secondary bracket 130 is formed of ceramic, plastic, metal, or polymer or in combination.

Figure 18:
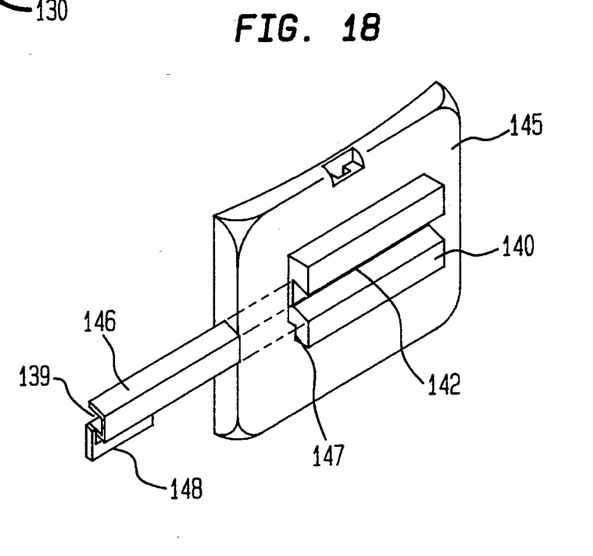
FIG. 18 is a perspective front elevational view of a bracket system assembly with a secondary bracket including an archwire with an attached detente.

FIG. 18 illustrates a detent 148 for holding a secondary bracket 146 in engagement with primary bracket 140. Detent 148 is received in slot 147 of primary bracket 145. Archwire slot 139 is formed within secondary bracket 146 and faces toward the tooth, whereby secondary bracket 146 can be locked in place without means for ligation.

Figure 19:
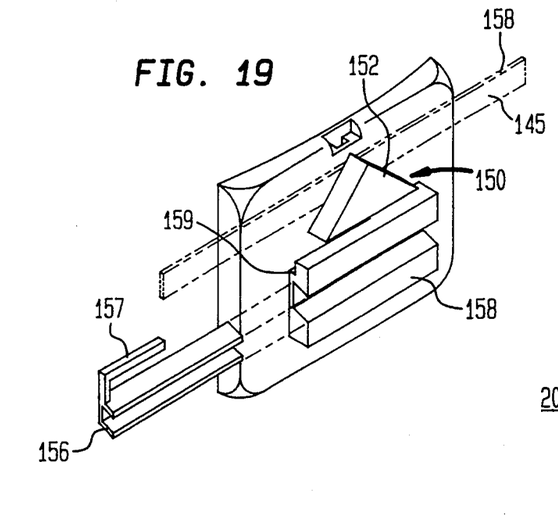
FIG. 19 is a perspective front elevational view of a bracket system assembly with a secondary bracket including a triangular shaped upper portion for holding a second archwire.

FIG. 19 illustrates an alternative embodiment of primary bracket 150 including upper triangular portion 152 for an auxiliary archwire 158. Horizontal slot 159 is formed on a wall of primary bracket 150. Secondary bracket 156 includes detent 157 which detent fits into slot 159 of primary bracket 150. Preferably, primary bracket 150 is used to include an additional archwire on a particular tooth.

Figure 20:
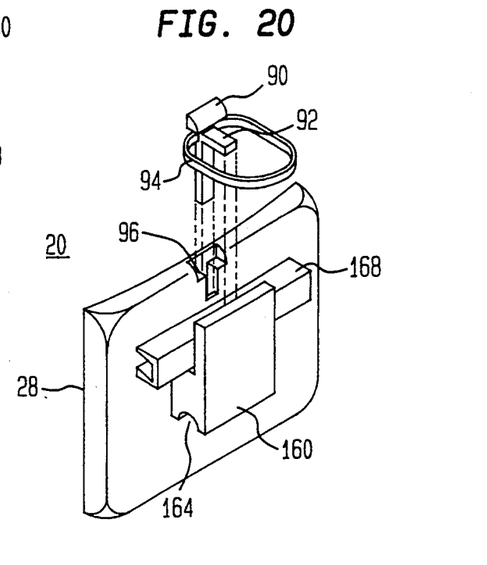
FIG. 20 is a perspective front elevational view of a bracket system assembly with a secondary bracket in combination with a Begg Bracket and including a pin ligature assembly.

FIG. 20 illustrates pin and ligation assembly 90 in combination with a conventional Begg bracket 160. Pin ligation assembly includes pin 92 and ligation 94. Pin 92 is received in vertical slot 96 of Begg bracket 160. A horizontal notch 164 is formed in Begg bracket 160 for receiving stretched ligation 94.

Figure 21:
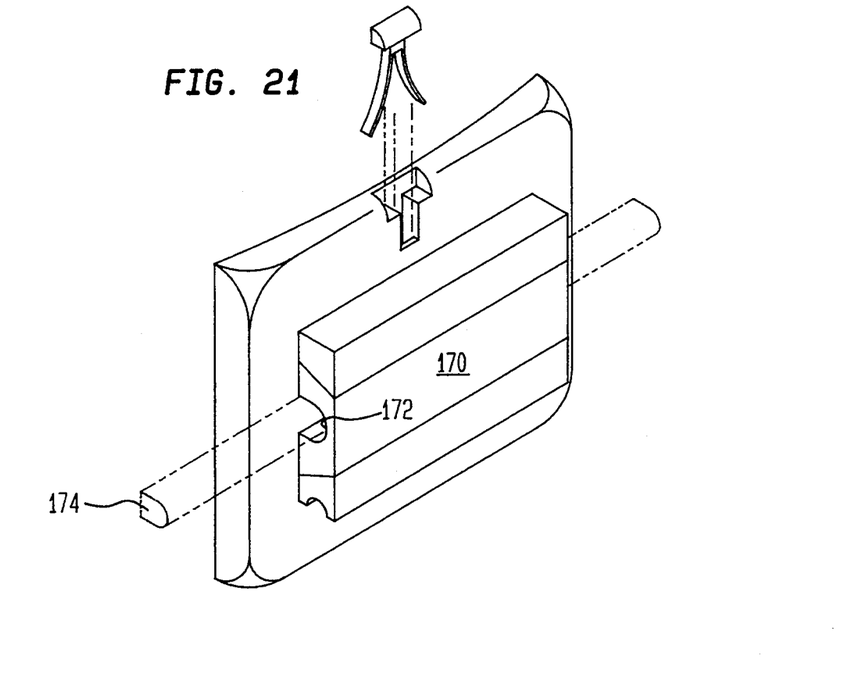
FIG. 21 is a front elevational view of a secondary bracket including an elliptically shaped archwire slot.

In an alternative configuration, secondary bracket 170 includes an archwire slot 172 having an elliptical shape, as shown in FIG. 21. Archwire 174 has a matching elliptical shape for fitting into archwire slot 172. Secondary bracket 170 has the advantage of providing less frictional resistance to the archwire after the archwire is engaged in the archwire slot.

Figure 22:
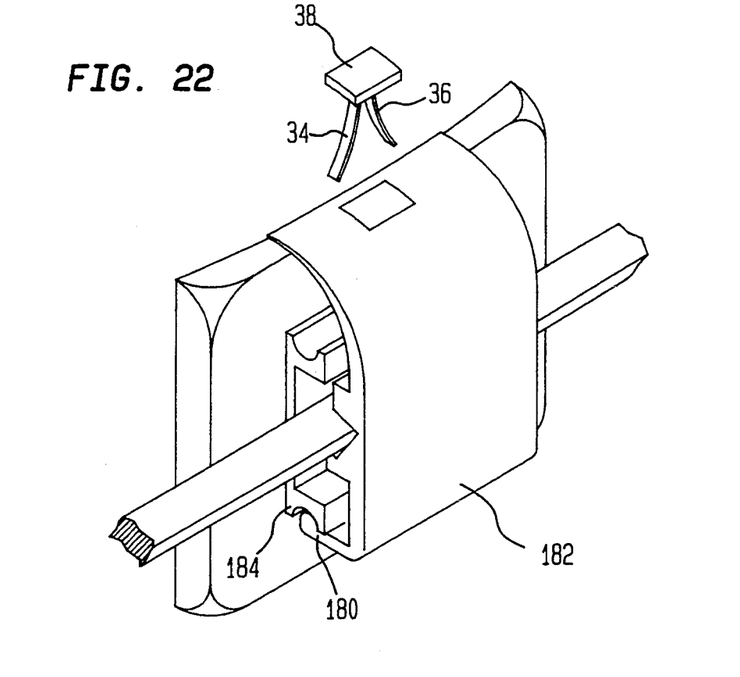
FIG. 22 is a perspective front elevational of a bracket system assembly with secondary bracket including an attachment flap connected to the primary bracket base held in place with a pin with biasing means in vertical slot.

FIG. 22 is an alternative arrangement of secondary bracket 180 including flap 182 attached to secondary bracket 180. Flap 182 snaps into engagement with primary bracket 184 and is held in place by pin 32 with legs 34 and 36.

Figure 23:
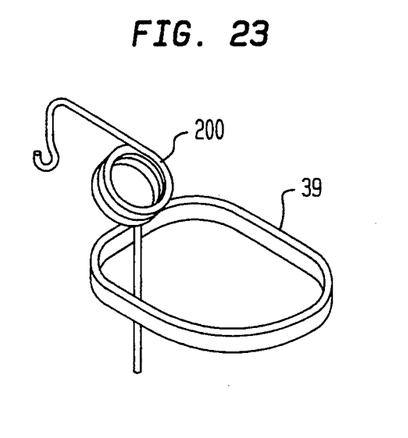
FIG. 23 is a perspective front elevational view of an uprighting spring pin including a ligature.

FIG. 23 is a side elevational view of an uprighting spring pin 200 used in combination with ligature 39. Uprighting spring pin 200 can be slid into vertical slot 30 and attached to primary bracket 12 with ligature 39, as shown in FIG. 1.

Figure 24:
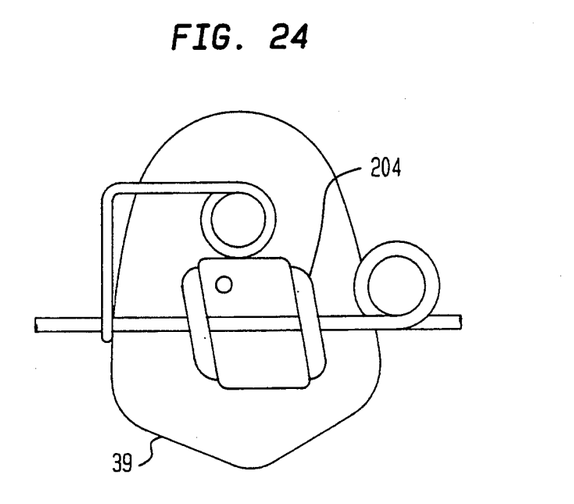
FIG. 24 is a top plan view of a counterclockwise uprighting spring pin including a ligature.
Figure 25:
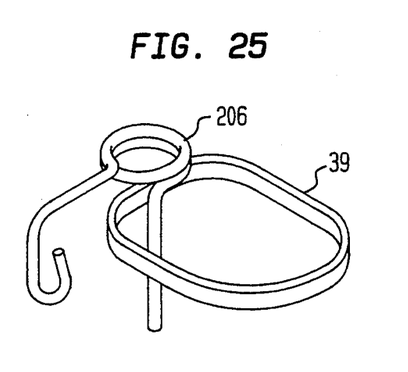
FIG. 25 is a perspective front elevational view of a rotating spring pin including a ligature.
Figure 26:
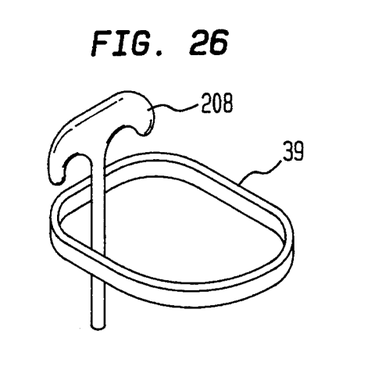
FIG. 26 is a perspective front elevational view of a power arm pin including a ligature.

FIG. 24 is a top plan view of an uprighting spring 204 including attached ligature 39. FIG. 25 illustrates a rotating spring pin 206 with attached ligature 39. A power arm pin 208 can also be used with ligature 39, as shown in FIG. 26. It will be appreciated from the teachings of the present invention that other attachments can be used with a ligature for locking the attachments in place. Conventional attachments have the disadvantage that one end of the attachment must be bent around the bracket to hold the attachment in place.

Figure 27:
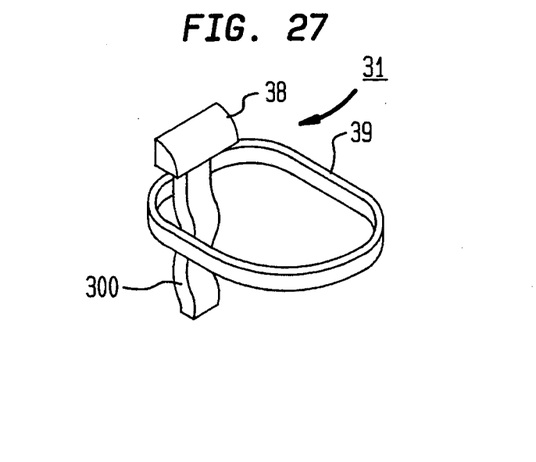
FIG. 27 is a perspective front elevational view of a pin and ligature assembly including a spring biasing means.

FIG. 27 illustrates a pin and ligature assembly 31 in which pin 300 has a curved shaped. Preferably, pin 300 is formed of a resilient material for biasing the pin and ligature assembly 31 into a vertical slot.

Orthodontic treatment is usually broken up into three stages. The orthodontic bracket of the present invention facilitates the treatment of teeth in all three stages by having the orthodontist choose a proper secondary bracket to correct the tooth problem at hand. In a first stage of treatment, teeth are unraveled and leveled and the goal is to establish a Class I molar, Class I cuspid relationship. That is, the orthodontist attempts to have the teeth in a straight and unrotated manner. This is accomplished by using a flexible archwire which is deflected from its original shape and by this flexible wire having memory it will move the teeth to the corrected position as the wire attempts to return to its original position. The same criteria are used for extraction and non-extraction cases. There are often times when extractions may be necessary so as to allow for the uncrowding of the teeth. The bracket assembly of the primary and the secondary bracket being of a certain configuration eliminates any further unwanted tipping of the teeth or tooth because of its broad engagement.

In stage one, for extraction cases, primary bracket 12 is attached to the tooth and archwire 44 is inserted into bracket assembly 10. Bracket assemblies which can be used in stage 1 include the assemblies shown in FIGS. 2–22.

In extraction cases the objectives of Stage Two are to close the extraction spaces while maintaining the already obtained objectives of Stage One; namely, Class I molar and cuspid relationship for both the upper and lower jaws. In non-extraction cases, after completion of Stage One, since there are no extractions, there is no Stage Two and treatment continues in Stage Three. The orthodontist can use bracket assemblies in Stage Two which are similar to the bracket assemblies used in Stage One. Secondary bracket configurations, as shown in FIGS. 3–22, can be used for angulating teeth to achieve a more favorable result before Stage Three of orthodontic treatment.

In Stage Three of orthodontic treatment, teeth are tipped and torqued into final desired position. As we previously stated, tipping of the teeth is the most gentle movement and forces applied to cause tipping tends to decrease any damage to the roots and surrounding bone and tissues of the teeth tipped. Examples of bracket assemblies useful for tipping teeth are shown in FIGS. 3, 4, 5, 6, 8, 11, 12, 13, 14A, 14B, 14C and 16. In Stage Three, uprighting and torquing forces are employed to put the crowns and roots of all teeth in their ideal position while still obtaining Class I maximum occlusion. In Stage Three of orthodontic treatment, a bracket assembly such as shown in FIGS. 3, 9, 11, 13, 14A, 14B, 14C, 6 and 20 is used for providing uprighting and torquing forces. In contrast, bodily movement such as with conventional wide edgewise brackets requires heavier forces to move the teeth into the desired position. Such heavier forces have been known to cause damage to the roots and surrounding bone and tissues of the anchor teeth and the teeth to be moved.

When using the bracket assembly of the present invention, a force is applied to the primary and secondary bracket and consequently to the tooth it is attached to and that same force can be exerted onto adjacent teeth. In an attempt to reduce the undesired forces on adjacent teeth, the archwires can include loops or have a special configuration. The archwires in conjunction with the predetermined angle of the archwire slot of the secondary bracket attached to adjacent teeth has the advantage of disposing any undesired forces to the adjacent teeth.

The bracket assemblies of the present invention have the advantage of providing tooth movement without wings ties so that there is less occlusal interference. In a preferred embodiment, the bracket assembly includes a first bracket attached to the tooth engaged with a secondary bracket. An archwire locks into the secondary bracket for eliminating the use of a ligation to hold the archwire in place. The archwire slot can be of various angulation for selective tooth movement. A novel pin and ligature assembly has the advantage biasing the assembly in a vertical slot of the bracket without bending the pin around the ligature.

While the invention has been described with reference to the preferred embodiment, this description is not intended to be limiting. It will be appreciated by those of ordinary skill in the art that modifications may be made without departing from the spirit and scope of the invention.

I claim:

1. An orthodontic bracket system for retaining an archwire in desired position with respect to the tooth of a patient whose teeth orientation is being corrected, said bracket system comprising:
   a primary bracket adapted to be fixed with respect to the surface of a tooth;
   a pair of spaced mesio-distally extending holding members on said primary bracket spaced to permit engagement of an arch wire therebetween;
   a slot extending into said primary bracket from an edge surface thereof;
   a spring pin member dimensioned for positioning within and spring biased into engagement with the sidewalls of said slot; and
   a cap member at the upper end of said spring pin.

2. An orthodontic bracket system as in claim 1 in which an elastic ligation is secured to the upper end of said spring pin member.

3. An orthodontic bracket system as in claim 1 in which a recess is formed in said primary bracket adjacent and surrounding the upper end of said slot of a dimension to accommodate said cap.

4. An orthodontic bracket system as in claim 1 in which said spring pin comprises a pair of outwardly biased spring legs.

5. An orthodontic bracket system as in claim 1 in which said spring pin comprises a rippled spring member in which the amplitude of the ripples is such as to cause the pin to extend across and frictionally engage between the sidewalls of said slot in said bracket member.

6. An orthodontic bracket system as in claim 1 in which a secondary bracket is engaged with said holding members, and an archwire receiving groove is formed in said secondary bracket open to said primary bracket, said groove dimensioned to enclose and arch wire between said primary and secondary brackets.

7. An orthodontic bracket system as in claim 6 in which said secondary bracket is formed with a front face covering said primary and secondary brackets when said brackets are assembled into said assembly.

8. An orthodontic bracket system as in claim 7 in which said front face is formed with a flap extending over the entry to said pin receiving slot, said flap formed with an opening aligned with the entry to said slot to receive said spring pin therethrough.

9. An orthodontic bracket system comprising: a primary bracket adapted to be fixed with respect to the surface of a tooth, said primary bracket having a detent receiving slot formed therein; a secondary bracket selectively securable to said primary bracket, said secondary bracket having an arch wire receiving slot extending horizontally across said secondary bracket; and a detent on said secondary bracket extending into the detent receiving slot of said primary bracket when said brackets are engaged.

10. An orthodontic bracket system for retaining an archwire in desired position with respect to the tooth of a patient whose teeth orientation is being corrected, said bracket system comprising:

a primary bracket adapted to be fixed with respect to the surface of a tooth;

a pair of spaced mesio-distally extending holding members on said primary bracket forming a slot therebetween, with engaging elements on the surface of said holding members opposite the slot;

a secondary bracket securable to said primary bracket;

spaced track elements on said secondary bracket engageable with the engaging elements on said primary bracket; and an archwire guiding block formed on said secondary bracket dimensioned to fit in the slot formed between said holding members on said primary bracket, said block having an archwire guiding opening extending therethrough through which an archwire may be threaded with the archwire surrounded.

* * * * *